(12) United States Patent
McCarthy et al.

(10) Patent No.: US 9,414,922 B2
(45) Date of Patent: Aug. 16, 2016

(54) THREE-DIMENSIONAL ANNULOPLASTY RING

(75) Inventors: Patrick M. McCarthy, Hunting Valley, OH (US); Richard S. Rhee, Anaheim Hills, CA (US); Stefan Schreck, Vista, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1226 days.

(21) Appl. No.: 13/370,228

(22) Filed: Feb. 9, 2012

(65) Prior Publication Data

US 2012/0143322 A1    Jun. 7, 2012

Related U.S. Application Data (60) Continuation of application No. 11/106,421, filed on Apr. 14, 2005, now Pat. No. 8,123,800, which is a division of application No. 10/139,070, filed on May 3, 2002, now Pat. No. 6,908,482, said application No.

(Continued)

(51) Int. Cl.
    *A61F 2/24*    (2006.01)
(52) U.S. Cl.
    CPC ............. *A61F 2/2466* (2013.01); *A61F 2/2445* (2013.01); *A61F 2/2448* (2013.01); *A61F 2230/0091* (2013.01); *A61F 2250/0029* (2013.01); *A61F 2250/0036* (2013.01); *A61F 2250/0037* (2013.01); *Y10S 623/90* (2013.01)
(58) Field of Classification Search
    CPC .............................. A61F 2/2445; A61F 2/2448
    See application file for complete search history.

(56) References Cited

U.S. PATENT DOCUMENTS

| | | |
|---|---|---|
| 3,656,185 A | 4/1972 | Carpentier |
| 4,055,861 A | 11/1977 | Carpentier et al. |
| 4,164,046 A | 8/1979 | Cooley |
| 4,217,665 A | 8/1980 | Bex et al. |
| 4,275,469 A | 6/1981 | Gabbay |
| 4,489,446 A | 12/1984 | Reed |

(Continued)

FOREIGN PATENT DOCUMENTS

| | | |
|---|---|---|
| EP | 0338994 A1 | 10/1989 |
| EP | 0595791 A2 | 5/1994 |

(Continued)

OTHER PUBLICATIONS

Adams, David, et al., "Large Annuloplasty Rings Facilitate Mitral Valve Repair in Barlow's Disease," Society of Thoracic Surgeons 42.sup.ndAnnual Meeting, Jan. 30-Feb. 1, 2006.

(Continued)

*Primary Examiner* — Thomas J Sweet
*Assistant Examiner* — Cheryl Miller
(74) *Attorney, Agent, or Firm* — Guy Cumberbatch; AnneMarie Kaiser; Pui Tong Ho (57) ABSTRACT

An annuloplasty ring having a three-dimensional discontinuous form generally arranged about an axis with two free ends that are axially offset. The ring is particularly suited for repair of the tricuspid valve, and more closely conforms to the annulus shape. The ring is more flexible in bending about radially extending axes than about the central axis. The ring may have an inner structural support covered by a pliable sleeve and/or a fabric tube. The structural support may have a varying cross-section, such as a C-shaped cross-section in a mid-section between two free ends and a rectangular cross-section at the free ends.

26 Claims, 7 Drawing Sheets

Related U.S. Application Data

13/370,228 is a continuation of application No. 12/102,789, filed on Apr. 14, 2008, now Pat. No. 8,114,155, which is a continuation of application No. 10/868,470, filed on Jun. 14, 2004, now Pat. No. 7,367,991, which is a continuation of application No. 10/139,070, filed on May 3, 2002, now Pat. No. 6,908,482, and a continuation-in-part of application No. 09/941,406, filed on Aug. 28, 2001, now Pat. No. 6,749,630.

(56) References Cited

U.S. PATENT DOCUMENTS

| | | |
|---|---|---|
| 4,602,911 A | 7/1986 | Ahmadi et al. |
| 4,790,844 A | 12/1988 | Ovil |
| 4,917,097 A | 4/1990 | Proudian et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,397,348 A | 3/1995 | Campbell et al. |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,368,348 B1 | 4/2002 | Gabbay |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,786,924 B2 | 9/2004 | Ryan et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,361,190 B2 | 4/2008 | Shaoulian et al. |
| 7,367,991 B2 | 5/2008 | McCarthy et al. |
| 7,527,647 B2 | 5/2009 | Spence |
| 7,608,103 B2 | 10/2009 | McCarthy |
| 7,959,673 B2 | 6/2011 | Carpentier et al. |
| 7,993,395 B2 | 8/2011 | Vanermen et al. |
| 8,123,800 B2 | 2/2012 | McCarthy et al. |
| 8,144,155 B2 | 3/2012 | Zhou et al. |
| 8,366,769 B2 * | 2/2013 | Huynh ............... A61F 2/2409 623/2.41 |
| 8,449,608 B2 * | 5/2013 | Brunnett ............. A61F 2/2445 623/2.36 |
| 8,460,173 B2 | 6/2013 | Schweich, Jr. et al. |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |

(56) References Cited

U.S. PATENT DOCUMENTS

| | | |
|---|---|---|
| 2005/0070999 A1 | 3/2005 | Spence |
| 2005/0075727 A1 | 4/2005 | Wheatley |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0129236 A1 | 6/2006 | McCarthy |
| 2006/0149368 A1 | 7/2006 | Spence |
| 2006/0195183 A1 | 8/2006 | Navia et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0287303 A1 | 11/2009 | Carpentier |

FOREIGN PATENT DOCUMENTS

| | | |
|---|---|---|
| EP | 0860151 A1 | 8/1998 |
| EP | 1034753 A1 | 9/2000 |
| EP | 1034753 B1 | 2/2005 |
| FR | 2708458 A1 | 2/1995 |
| WO | 9119456 A1 | 12/1991 |
| WO | 9503757 A1 | 2/1995 |
| WO | 9640006 A1 | 12/1996 |
| WO | 9741801 A1 | 11/1997 |
| WO | 9742871 A1 | 11/1997 |
| WO | 9806329 A1 | 2/1998 |
| WO | 9911201 A2 | 3/1999 |
| WO | 99/49816 A1 | 10/1999 |
| WO | 9951169 A1 | 10/1999 |
| WO | 9965423 A1 | 12/1999 |
| WO | 0032105 A1 | 6/2000 |
| WO | 0119292 A1 | 3/2001 |
| WO | 0126586 A1 | 4/2001 |
| WO | 0147438 A1 | 7/2001 |
| WO | 0187191 A1 | 11/2001 |
| WO | 0203892 A1 | 1/2002 |
| WO | 03020178 A1 | 3/2003 |
| WO | 03041617 A1 | 5/2003 |
| WO | 2004/004607 A1 | 1/2004 |
| WO | 2005/004753 A1 | 1/2005 |
| WO | 2005/034813 A2 | 4/2005 |
| WO | 2005/082278 A2 | 9/2005 |
| WO | 2005/110290 A1 | 11/2005 |
| WO | 2006/041877 A2 | 4/2006 |
| WO | 2006/133186 A2 | 12/2006 |
| WO | 2007-050506 A1 | 5/2007 |
| WO | 2007/100408 A2 | 9/2007 |
| WO | 2007/131513 A1 | 11/2007 |
| WO | 2008/058940 A1 | 5/2008 |
| WO | 2008/063537 A2 | 5/2008 |
| WO | 2008/094469 A2 | 8/2008 |
| WO | 2008/098226 A1 | 8/2008 |

OTHER PUBLICATIONS

Alonso-Lei, MD., et al., Adjustable Annuloplasty for Tricuspid Insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Caleya, et al., Fracture of Carpenter's Ring in a Patient with Tricuspid Annuloplasty. Thoracic Cardiovascular Surgeon. vol. 31. pp. 175-176. 1983.

Carpentier, et al. "The 'Physio-Ring': An Advanced Concept in Mitral Valve Annuloplasty," Society of Thoracic Surgeons 31.sup.st Annual meeting, Jan. 30-Feb. 2, 1995.

Carpentier, et al., Reconstructive Valve Surgery, Chapters 17-19, ISBN No. 978-0-7216-9168-8, Sanders Elsevier Publishing, Maryland Heights, Missouri, 2010.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5155-5161, 1998.

Cosgrove, et al., Initial Experience with the Cosgrove-Edwards Annuloplasty System. The Annals of Thoracic Surgery. vol. 60. pp. 499-504. 1995.

Cosgrove-Edwards, Annuloplasty System. Edwards Lifesciences Corporation. 2000.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Galinanes, et al., Fracture of the Carpentier-Edwards Ring in Tricuspid Position: A Report of Three Cases. The Annals of Thoracic Surgery. vol. 42. pp. 74-76. 1986.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Navia, Jose Luis., Minimally Invasive Mitral Valve Surgery. Department of Thoracic and Cardiovascular Surgery, The Cleveland Clinic Foundation. 2001.

Qin, et al., Validation of Real-Time Three-Dimensional Echocardiography for Quantifying Left Ventricular Volumes in the Presence of a Left Ventricular Aneurysm: In Vitro and In Vivo Studies. Journal of the American College of Cardiology. vol. 36. No. 3. ISSN 0735-1097. pp. 900-907. 2000.

(56) References Cited

OTHER PUBLICATIONS

Salgo, et al., Effect of Annular Shape on Leaflet Curvature in Reducing Mitral Leaflet, American Heart Association, Circulation 2002; 106 (6): 711, printed Oct. 28, 2003, 16pgs.

Seguin, et al., Advance in Mitral Valve Repair Using a Device Flexible in Three Dimensions, The St. Jude Medical-Seguin Annuloplasty Ring, Asaio Journal, vol. 42, No. 6, pp. 368-371, 1996.

Smolens, et al., Mitral Valve Repair in Heart Failure, The European Journal of Heart Failure 2, pp. 365-371,2000.

Techniques for 3D Quantitative Echocardiography, University of Washington Cardiovascular Research & Training Center Cardiac Imaging Research Lab, pp. 1-5, Oct. 2003.

Watanbe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association .CO PVRGT.2005; ISSN: 1524-4539.

* cited by examiner

THREE-DIMENSIONAL ANNULOPLASTY RING

RELATED APPLICATIONS

The present application is a continuation of application Ser. No. 11/106,421, filed Apr. 14, 2005, now U.S. Pat. No. 8,123,800, which is a divisional of application Ser. No. 10/139,070, filed May 3, 2002, now U.S. Pat. No. 6,908,482; the present application is also a continuation of U.S. application Ser. No. 12/102,789, filed Apr. 14, 2008, now U.S. Pat. No. 8,114,155, which is a continuation of U.S. application Ser. No. 10/868,470, filed Jun. 14, 2004, now U.S. Pat. No. 7,367,991, which is a continuation of U.S. application Ser. No. 10/139,070, filed May 3, 2002, now U.S. Pat. No. 6,908,482, and a continuation-in-part of U.S. application Ser. No. 09/941,406 filed Aug. 28, 2001, now U.S. Pat. No. 6,749,630.

FIELD OF THE INVENTION

The present invention relates generally to medical devices and particularly to a tricuspid annuloplasty ring and delivery template.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques may be used to repair a diseased or damaged valve. In a valve replacement operation, the damaged leaflets are excised and the annulus sculpted to receive a replacement valve.

Another less drastic method for treating defective valves is through repair or reconstruction, which is typically used on minimally calcified valves. One repair technique that has been shown to be effective in treating incompetence is annuloplasty, in which the effective size of the valve annulus is contracted by attaching a prosthetic annuloplasty repair segment or ring to an interior wall of the heart around the valve annulus. The annuloplasty ring is designed to support the functional changes that occur during the cardiac cycle: maintaining coaptation and valve integrity to prevent reverse flow while permitting good hemodynamics during forward flow. The annuloplasty ring typically comprises an inner substrate of a metal such as stainless or titanium, or a flexible material such as silicone rubber or Dacron cordage, covered with a biocompatible fabric or cloth to allow the ring to be sutured to the heart tissue. Annuloplasty rings may be stiff or flexible, may be split or continuous, and may have a variety of shapes, including circular, D-shaped, C-shaped, or kidney-shaped. Examples are seen in U.S. Pat. Nos. 5,041,130, 5,104,407, 5,201,880, 5,258,021, 5,607,471 and, 6,187,040 B1. Most annuloplasty rings are formed in a plane, with some D-shaped rings being bowed along their anterior or straight side to conform to the annulus at that location.

The present application has particular relevance to the repair of tricuspid valve, which regulates blood flow between the right atrium (RA) and right ventricle (RV), although certain aspects may apply to repair of other of the heart valves.

Figure 1:
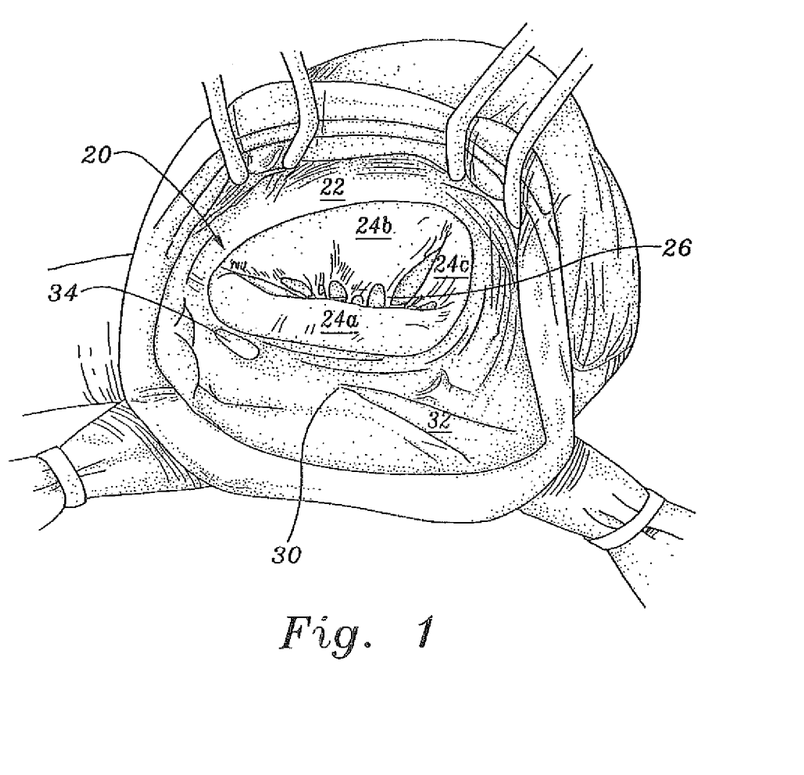
FIG. 1 is a plan view of the tricuspid valve and surrounding anatomy.

The tricuspid valve 20 is seen in plan view in FIG. 1 and includes an annulus 22 and three leaflets 24a, 24b, 24c (septal, anterior, and posterior, respectively) extending inward into the flow orifice defined by the annulus. Chordae tendineae 26 connect the leaflets to papillary muscles located in the RV to control the movement of the leaflets. The tricuspid annulus 22 is an ovoid-shaped fibrous ring at the base of the valve that is less prominent than the mitral annulus, but slightly larger in circumference. The septal leaflet 24a is the site of attachment to the fibrous trigone, the fibrous "skeletal" structure within the heart. The triangle of Koch 30 and tendon of Todaro 32 provide anatomic landmarks during tricuspid valve repair procedures. The atrioventricular (AV) node 34 is a section of nodal tissue that delays cardiac impulses from the sinoatrial node to allow the atria to contract and empty their contents first, and relays cardiac impulses to the atrioventricular bundle. In a normal heart rhythm, the sinoatrial node generates an electrical impulse that travels through the right and left atrial muscles producing electrical changes which is represented on the electrocardiogram (ECG) by the p-wave. The electrical impulse then continues to travel through the specialized tissue of the AV node 34, which conducts electricity at a slower pace. This will create a pause (PR interval) before the ventricles are stimulated. Of course, surgeons must avoid placing sutures too close to or within the AV node 34. C-rings are good choices for tricuspid valve repairs because they allow surgeons to position the break in the ring adjacent the AV node 34, thus avoiding the need for suturing at that location.

Despite numerous designs presently available or proposed in the past, there is a need for a tricuspid ring that more closely conforms to the actual shape of the tricuspid annulus.

SUMMARY OF THE INVENTION

The present invention provides an annuloplasty ring including a ring body generally arranged about an axis and being discontinuous so as to define two free ends. The ring body has a relaxed configuration following a three-dimensional path such that the free ends are axially offset from an annulus reference plane through a midpoint of the ring body. In a preferred embodiment, the two free ends are axially offset between about 2-15 mm. The annuloplasty ring is particularly adapted to reinforce the tricuspid annulus, and as such has a curvilinear anterior side ending in one of the free ends, a curvilinear posterior side ending in the other of the free ends, and a relatively straight septal side extending between the anterior and posterior sides. The posterior side is shorter and has a smaller radius of curvature than the anterior side.

In accordance with one aspect of the present invention, the ring body comprises an inner structural support of multiple bands of elastic material. A low friction material may be interposed between each two adjacent bands to facilitate movement therebetween. The multiple bands may be embedded in a matrix of pliable material, preferably molded silicone. In one embodiment, there are two concentrically disposed bands embedded in the matrix of pliable material. To facilitate bending about axes that extend radially, each of the multiple bands of elastic material may have a relatively wider radial dimension than its axial dimension.

Another aspect of the invention is an annuloplasty ring that comprises a three-dimensional ring body generally arranged about a central axis and being discontinuous so as to define two free ends, wherein the ring body has a construction that renders it more flexible in bending at the two free ends than in a midpoint thereof.

The annuloplasty ring body may comprise an inner structural support having two free ends, a curvilinear anterior side ending in one of the free ends, a relatively straight septal side ending in the other of the free ends, and a curvilinear posterior side extending between the anterior and septal sides, wherein a majority of the posterior side lies generally in a plane perpendicular to the axis. The two free ends are desirably both axially offset in the same direction from the plane. Also, the structural support may have a cross-section that changes around its length. For example, the cross-section may be partly C-shaped in the posterior side, yet the two free ends are rectangular.

In accordance with a further aspect of the invention, the ring body may comprise an inner structural support band surrounded by a pliable matrix, wherein the matrix includes a tubular inner portion that surrounds the band and an outer flange through which implantation sutures can pass. The outer flange may be curved so as to be convex on its outer surface. Preferably, the outer flange is connected to the inner tubular portion with a plurality of circumferentially spaced apart radial walls so as to create a celled structure.

A further aspect of the present invention provides an annuloplasty ring including a ring body generally arranged about the central axis and being discontinuous so as to define two free ends. The ring body has a construction that renders it more flexible in bending about axes that extend radially from the central axis than about the central axis itself. The ring body may comprise an inner structural support of multiple bands of elastic material. A low friction material may be interposed between each two adjacent bands. The multiple bands may be embedded a matrix of pliable material, preferably silicone. There may be two concentrically disposed bands embedded in the matrix of pliable material. Desirably, each of the multiple bands elastic material has a relatively wider radial dimension than its axial dimension.

In a still further aspect of the present invention, an annuloplasty ring template is provided. The template has a rigid body with a peripheral mounting ring generally arranged about an axis and being discontinuous so as to define two free ends. The mounting ring follows a three-dimensional path such that the free ends are axially offset. The template may include a central platform to which the peripheral mounting ring is connected via a plurality of generally radially extending spokes. A handle-receiving hub may extend generally away from central platform. Desirably, the peripheral mounting ring extends about three-quarters circumferentially about the axis.

In a preferred embodiment, the peripheral mounting ring of the template defines a radially outward groove therein for receiving an annuloplasty ring. The template further may include a plurality of cutting guides provided on the peripheral mounting ring. A pair of through holes in the mounting ring are provided on either side of each cutting guide such that a length of suture may extend through or about an annuloplasty ring positioned on the outside of the mounting ring, through one of the holes, over the cutting guide, through the other hole, and back into the annuloplasty ring. Each cutting guide may comprise a pair of intersecting slots, one of the slots being shallower than the other and positioned to receive a suture extending between the through holes. The deeper slot provides space into which a sharp instrument may extend to sever the suture at the cutting guide.

Further understanding of the nature and advantages of the invention will become apparent by reference to the remaining portions of the specification and drawings.

DESCRIPTION OF THE PREFERRED EMBODIMENTS

The present invention provides a non-planar or three-dimensional (3D) annuloplasty ring that is shaped to conform to a 3D annulus. Some studies show that the tricuspid valve has such a non-planar annulus, and thus the present invention is particularly suited for repair of that valve. Of course, other valves may in some patients have 3D annuluses, and the annuloplasty ring of the present invention may also have use in those locations, if desired by the surgeon. Of course, all annuloplasty rings are three-dimensional to some extent, as they have a cross-sectional thickness. In the context of the present invention, a non-planar or three-dimensional annuloplasty ring has a nominal cross-sectional centerline that assumes a three-dimensional shape, or in other words does not lie in a single plane. Likewise, the exemplary ring of the present invention, as well as other shapes that may benefit from the features embodied herein, has a non-circular peripheral shape, but is shown having an axis. The term "axis" in reference to the illustrated ring, and other non-circular or non-planar rings, refers the line through the ring that passes through the area centroid of the ring when viewed in plan view. This "axis" can also be viewed as imaginary line of blood flow within the valve orifice and thus within the ring when implanted therein.

It should be understood that the various constructional details of any one embodiment herein may be transferred to another embodiment, even if not explicitly mentioned. For instance, the inner ring structural support seen in FIGS. 8A-8D may be used in a ring that has a silicone sleeve and outer fabric covering as described elsewhere. Also, the templates 90 or 110 seen in FIGS. 5-7 may be adapted to conform to and hold the ring constructed using the inner ring structural support seen in FIGS. 8A-8D.

Despite numerous ring designs in the past, none has effectively accommodated the shape of the tricuspid valve. Prior C-shaped rings (i.e., those with a break in continuity around the periphery) are formed in a plane. When implanted, a planar ring will tend to conform a non-planar annulus to its own shape because of its relative stiffness. Unfortunately, this may interfere with optimum performance of the "repaired" valve.

Figure 2:
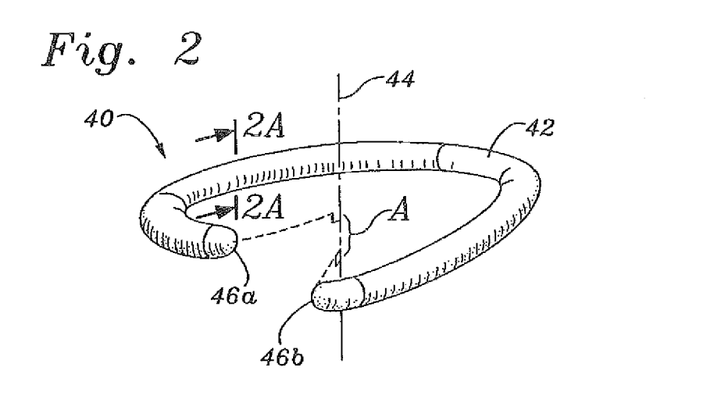
FIG. 2 is a perspective view of an exemplary annuloplasty ring of the present invention illustrating its axially-spaced free ends.
Figure 3:
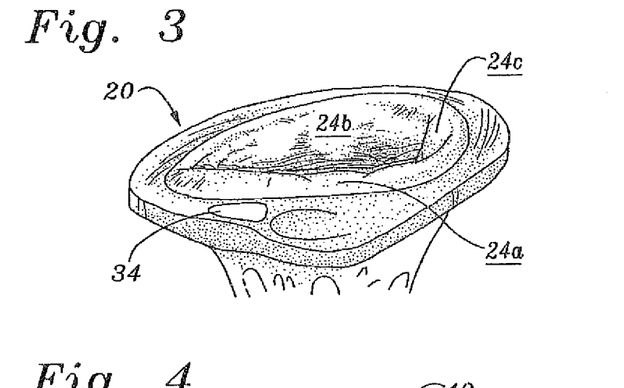
FIG. 3 is a perspective view of a tricuspid valve and surrounding anatomy.
Figure 4:
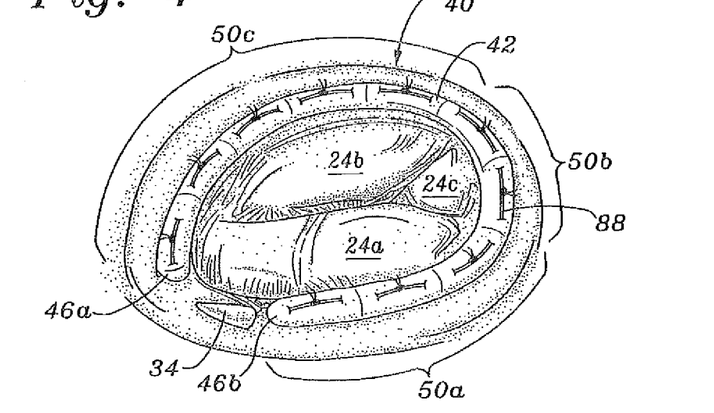
FIG. 4 is a plan view of the annuloplasty ring of FIG. 2 implanted around the tricuspid valve.

FIG. 2 illustrates an exemplary annuloplasty ring 40 of the present invention having a ring body 42 generally arranged about an axis 44 and being discontinuous so as to define two free ends 46a, 46b. FIG. 3 shows a tricuspid valve 20 in perspective, and FIG. 4 shows the annuloplasty ring 40 in plan view after having been implanted or otherwise affixed to the tricuspid valve 20. When viewed in plan view, as seen in FIG. 4, the body 42 of the annuloplasty ring 40 defines a relatively straight septal side 50a, a curvilinear posterior side 50b, and a curvilinear anterior side 50c. The posterior side 50b is shorter and has a smaller radius of curvature than the anterior side 50c.

Again, the axis 44 in FIG. 2 lies at the centroid of the ring or along of the axis of blood flow through the ring 40 when implanted, and it will be understood that the directions up and down are as viewed in the figure. The ring 40 is designed to be implanted in a tricuspid annulus such that blood will flow in the downward direction.

FIG. 2 illustrates an exemplary axial offset of the two free ends 46a, 46b. Radial lines are shown from each free end 46a, 46b to the central axis 44. The distance A between the intersections of these radial lines and the axis 44 represents the axial offset. The distance A may vary depending on the patient, but is typically between about 2.0 mm and 15.0 mm. In this embodiment, the curvilinear anterior side 50c lies generally in a plane all the way to the free end 46a. Therefore, because the second free end 46b drops below the main part of the anterior side 50c, which generally defines an annulus reference plane for the ring and host annulus, then it is axially offset from the first free end 46a. However, the first free end 46a may not lie in the annulus reference plane, and may drop to the same elevation as the second free end 46b. Either free end 46a, 46b may even be axially above the annulus reference plane. In short, the ring 40 is designed to be three-dimensional to conform to the native tricuspid annulus, and those of skill in the art will recognize the number of possible permutations.

Figure 2A:
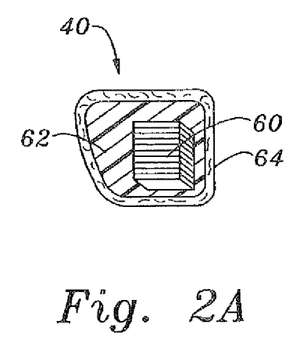
FIG. 2A is a cross-sectional view of the exemplary annuloplasty ring taken along line 2A-2A of FIG. 2.

Although the annuloplasty ring 40 may be constructed in a number of ways as defined in the prior art, one particularly useful construction includes some relatively rigid yet elastic inner structural support surrounded by a pliable core material and a fabric cover. For example, as seen in FIG. 2A, the annuloplasty ring 40 may include an inner skeleton of multiple bands 60 of relatively rigid yet elastic material such as Elgiloy surrounded by a suture-permeable core material 62 such as silicone, and having an outer fabric cover 64. The multiple bands 60 may be separated by plastic or other relatively low friction material (e.g., TEFLON) so as to be able to more easily flex with respect to one another. It will be noted by those of skill in the art that the multiple bands 60, which limit the flexibility of the ring 40, are aligned generally perpendicular to the axis 44 and thus the ring is least flexible in bending about the axis. Desirably, the ring 40 of the present invention is more flexible in bending about axes along radial lines from the central axis 44. That is, for example, the free ends 46a, 46b are more easily flexed up and down parallel to the axis than toward or away from one another. There are a number of ways to accomplish this flexibility orientation, as seen in FIGS. 2C-2E.

Figure 2B:
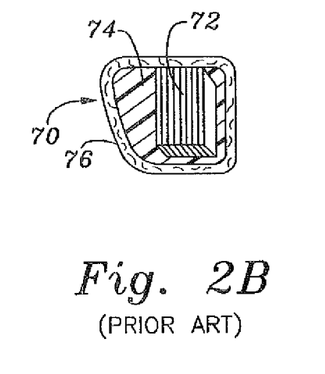
FIG. 2B is a cross-sectional view similar to FIG. 2A of an annuloplasty ring of the prior art.

In contrast, FIG. 2B shows a cross-section of a ring 70 of the prior art that has an inner skeleton of multiple bands 72 of relatively rigid material such as Elgiloy surrounded by a suture-permeable core material 74 such as silicone, with an outer fabric cover 76. In such prior devices, the bands 60 are oriented along or parallel to the axis 44, and thus are more flexible in bending about the central axis.

Figure 2C:
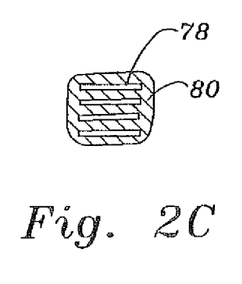
FIGS. 2C-2E are cross-sectional views of alternative annuloplasty rings of the present invention taken through the rings in the same location as line 2A-2A of FIG. 2.

FIG. 2C shows a cross-section of an alternative ring of the present invention having a plurality of inner bands 78 embedded in a more pliable matrix 80 such as silicone. As before, the bands 78 are desirably more rigid than the matrix 80 and provide structural support to the annulus when implanted. The bands 78 are thin in the axial dimension, and wide in the radial direction, so as to provide the preferred flexibility characteristics of the ring of the present invention. The bands 78 are shown spaced apart with matrix 80 material therebetween to enhance the aforementioned flexibility.

Figure 2D:
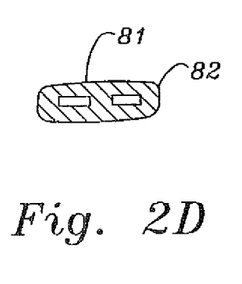
Figure 2E:
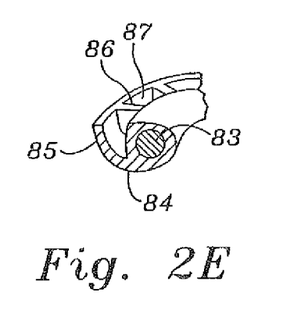

FIG. 2D illustrates a further embodiment in which there are two concentrically disposed structural bands 81 embedded in a matrix 82 of pliable material. The bands 81 together create the desired flexibility characteristics of the ring, as explained above, even if their respective cross-sections are square or circular. As seen, however, the bands 81 preferably have a larger radial than axial dimension which contributes to the flexibility of the ring about radial axes.

FIG. 2E shows a cross-section of a ring having a circular reinforcing band 83 surrounded by a pliable matrix 84. A tubular inner portion of the matrix 84 surrounds the band 83, while an outer wall or flange 85 provides additional material through which implantation sutures can pass. In a preferred embodiment, the flange 85 is curved so as to be convex on its outer surface, and is connected to the inner tubular portion with a plurality of circumferentially spaced apart radial walls 86. A series of circumferential cells 87 is thus created between the walls 86. The celled structure of the matrix 84 renders it soft and compressible, which facilitates conformance of the ring to very uneven annuluses. A fabric covering (not shown) may also be used.

With reference again to FIGS. 2 and 3, the three-dimensional shape of the annuloplasty ring 40 is seen corresponding generally to the shape of the tricuspid annulus 22. The first free end 46a registers with an area adjacent the septal leaflet 24a, to the anterior side of the AV node 34. The second free end 46b registers with an area adjacent the septal leaflet 24a, but to the posterior side of the AV node 34. The second free end 46b is axially offset with respect to the first free end 46a as is the respective anatomical attachment areas. Therefore, the annuloplasty ring 40 closely conforms to the 3-D shape of the annulus 22, and minimal distortion of the tissue occurs when attaching the ring thereto. Furthermore, the oriented flexibility of the ring 40 facilitates the 3-D shape matching, between ring and tissue because the free ends 46a, 46b may be easily flexed with respect to one another along arcs that are generally parallel to the axis 44.

The annuloplasty ring 40 is seen in FIG. 4 implanted in the annulus 22 using a plurality of sutures 88, although those of skill in the art will understand that there are other attachment means. The sutures 88 are evenly distributed around the ring body 42 and tied off to present minimal surface roughness and reduce the chance of thrombi forming thereon. Again, the free ends 46a, 46b are shown on either side of the AV node 34, which minimizes the risk of damaging the sensitive conduction system.

Figure 5:
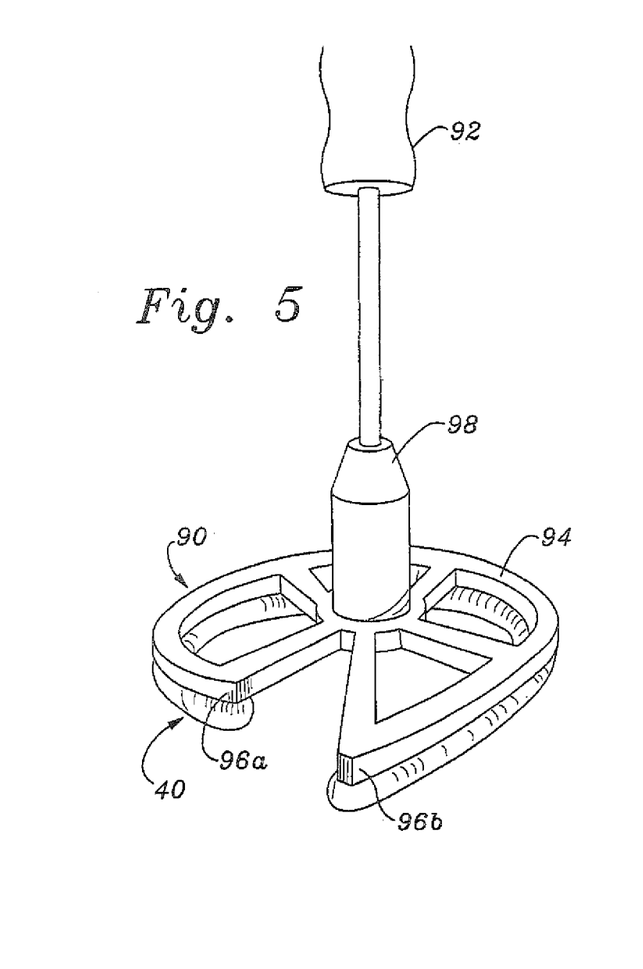
FIG. 5 is a perspective view of exemplary annuloplasty ring, holder template and delivery handle of the present invention.
Figure 6:
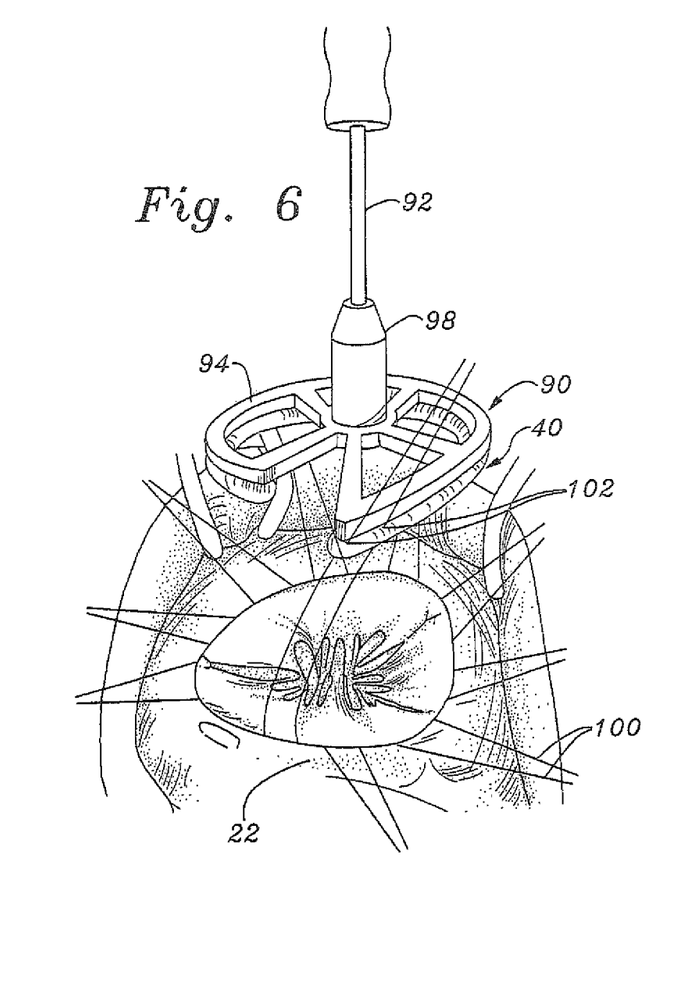
FIG. 6 is a perspective view of the ring, template and handle combination of FIG. 5 positioned above the tricuspid valve and showing an exemplary attachment method.

A preferred delivery template and method are also provided for the three-dimensional annuloplasty ring 40 of the present invention. With reference to FIGS. 5 and 6, the ring 40 is shown releasably secured to a template 90 that is in turn held at the distal end of a delivery handle 92. The template 90 provides a suturing platform for the ring 40, maintaining its advantageous shape while being implanted. In this regard, the template 90 includes a peripheral mounting ring 94 generally arranged about an axis coincident with the axis 44 of the ring 40. The peripheral mounting ring 94 is discontinuous so as to define two free ends 96a, 96b and generally follows a three-dimensional path such that the free ends are axially offset. Desirably, the three-dimensional path of the peripheral mounting ring 94 is the same as that of the annuloplasty ring 40. Sutures (not shown) or other similar expedient releasably secure the ring 40 to the template 90 to form the assembly seen in FIG. 5. A hub 98 of the handle 92 may be releasably attached to the template using sutures or quick-release clips or the like so that the handle may be removed during implantation for better visibility of the annulus.

FIG. 6 shows a step in an interrupted suture implant procedure. After exposing the annulus 22, the surgeon secures a plurality of individual sutures 100 around the annulus 22 in the locations that the sutures will be arranged around the ring 40. The free ends of each suture 100 are then passed through the corresponding positions in the suture-permeable outer portion of the ring 40, as seen at 102. After all of the sutures 100 have been pre-threaded through the ring 40, the surgeon manipulates the ring using the handle 92 down the array of sutures and into position in the annulus 22. The next steps that are not illustrated include severing each suture close to the ring 40 and tying them off as seen in FIG. 4. Again, the handle 92 may be detached from the template 90 for this operation. Finally, the template 90 is detached from the ring 40 and removed with any attaching sutures from the operating site.

Figures 7A, 7C:
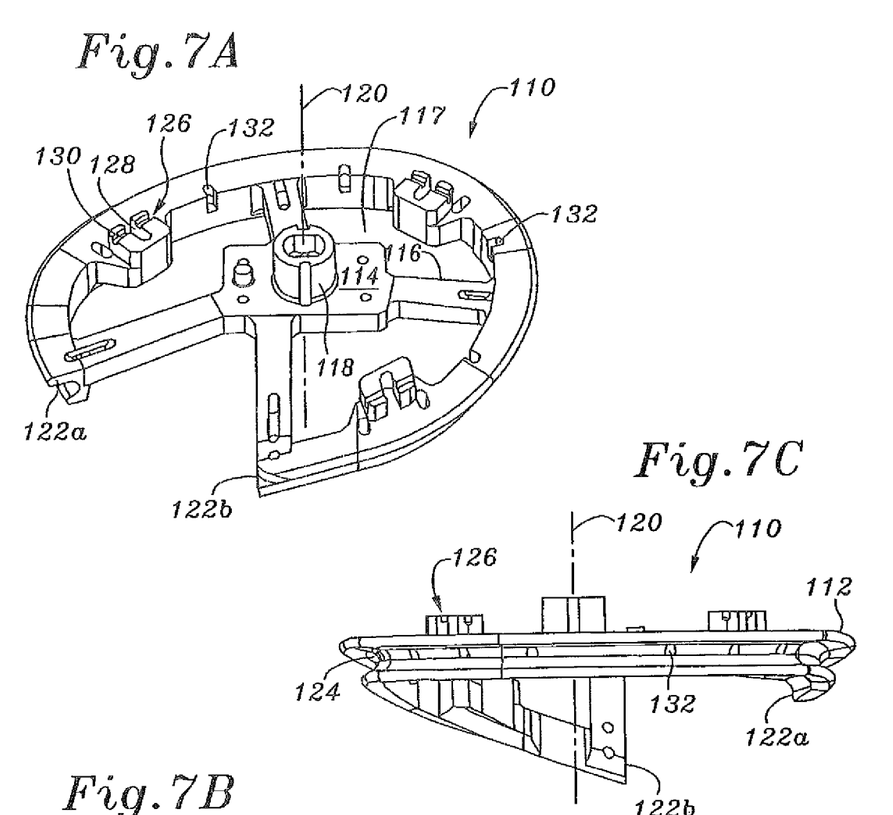
FIGS. 7A-7C are perspective and elevational views of a further exemplary holder template of the present invention.
Figure 7B:
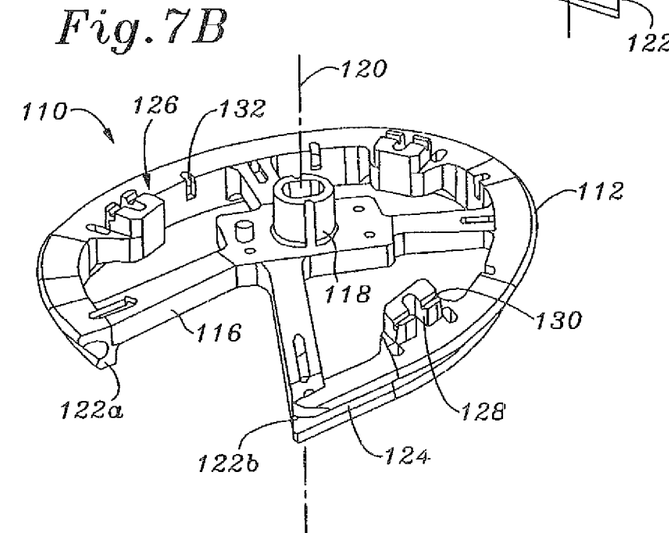

FIGS. 7A-7C are several perspective views of an exemplary template 110 for use in implanting the ring 40 of the present invention. The template 110 includes a peripheral mounting ring 112 connected to a central platform 114 via a plurality of spokes 116. The template 110 may be constructed of a variety of materials, with a biocompatible plastic being preferred. Windows 117 exist between the spokes 116 for greater visibility of the implant site. A handle-receiving hub 118 projects upward from the platform 114 and generally defines a central axis 120 of the template 110. The mounting ring 112 extends approximately three-quarters around the axis 120 and terminates in two axially-spaced free ends 122a, 122b.

In a preferred embodiment, the mounting ring 112 includes a radially outwardly opening channel or groove 124, which is sized to have about the same curvature as the ring 40, and thus snugly retains the ring 40 in place around the template 90. The groove 124 is shallow so that a majority of the ring projects outward therefrom to facilitate exposure to the annulus and attachment thereto.

A plurality, preferably three, of cutting guides 126 projects axially upward from the mounting ring 112 at regular intervals around its periphery. The cutting guides 126 each include a first relatively deep slot 128 and a second shallower slot 130 crossing the first slot. Sutures (not shown) desirably fasten the ring 40 to the template, and extend across the cutting guides 126 for easy severability. A plurality of passages 132 in the mounting ring 112 opening in the groove 124 permit passage of sutures directly from the ring body 42 through the mounting ring to the cutting guides 126. As seen best in FIG. 7A, there are two such passages 132 on either side of each cutting guide 126. The passages 132 are desirably straight holes from the upper surface of the mounting ring 112 that intersect and thus open to the concave groove 124.

The overall shape of the mounting ring 112 is three-dimensional, as explained above, with the two free ends 122a, 122b being axially spaced apart. The three-dimensional may be a gentle spiral, or other similar shape as dictated by the particular patient, or by a representative sample of patients. In the illustrated embodiment, and as best seen in FIG. 7C, a majority of the mounting ring 112 lies in a plane, with one side that terminates in the second free end 122b being formed in a gentle curve or spiral so as to be axially spaced from the first free end 122a. The annuloplasty ring is arranged on the mounting ring 112 so that the portion that will lie adjacent the septal leaflet (see 24a and 50a in FIG. 4) extends along the spiral segment of the mounting ring. In general, it is believed that many patients have a relatively planar tricuspid annulus around the anterior and posterior sides, but a depressed septal side. The shape of the mounting ring 112 thus mimics the presumed anatomical contour, and thus the ring can be sewn into place without unduly distorting the annulus.

FIGS. 8A-8D illustrate an exemplary inner structural support 150 for a tricuspid annuloplasty ring of the present invention. The structural support 150 is ultimately is covered with one or more outer flexible layers as described above, and therefore the final ring body assumes the shape of the support. The structural support 150 may be made of a relatively rigid material yet elastic material such as Elgiloy.

Figure 8A:
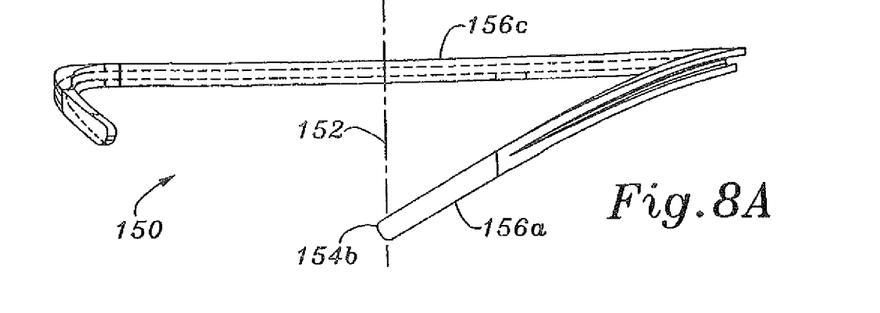
FIGS. 8A-8D are perspective, elevational and plan views of a rigid yet elastic inner structural support of an alternative annuloplasty ring of the present invention.
Figure 8B:
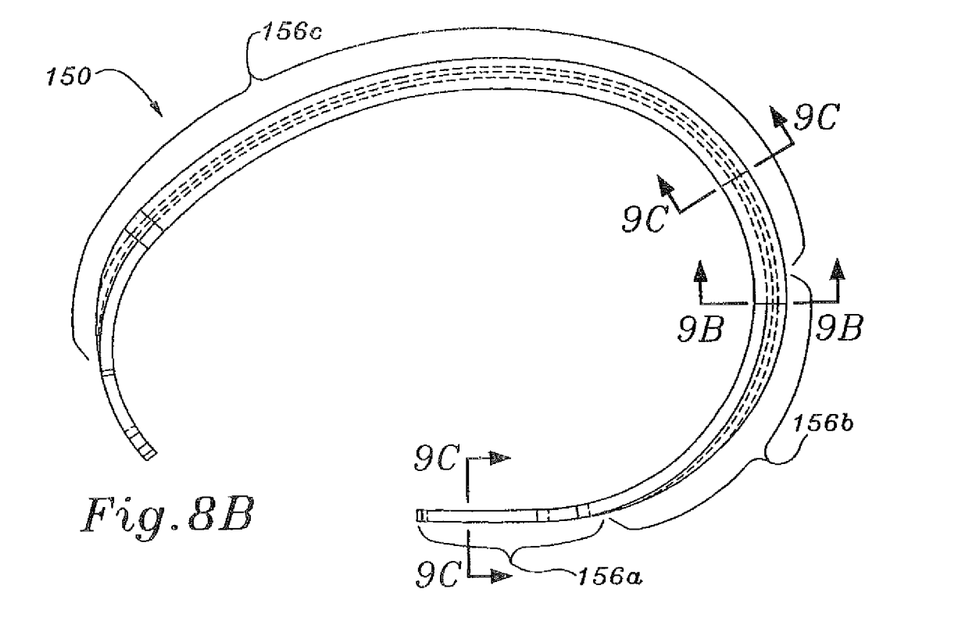

When viewed in plan view, as seen in FIG. 8B, the structural support 150 defines a relatively straight septal side 156a ending in one of the free ends 154b, a curvilinear posterior side 156b, and a curvilinear anterior side 156c ending in the other of the free ends 154a. The posterior side 156b is between the other two sides. As in the earlier embodiment, the posterior side 156b is shorter and has a smaller radius of curvature than the anterior side 156c.

Figures 8C, 8D:
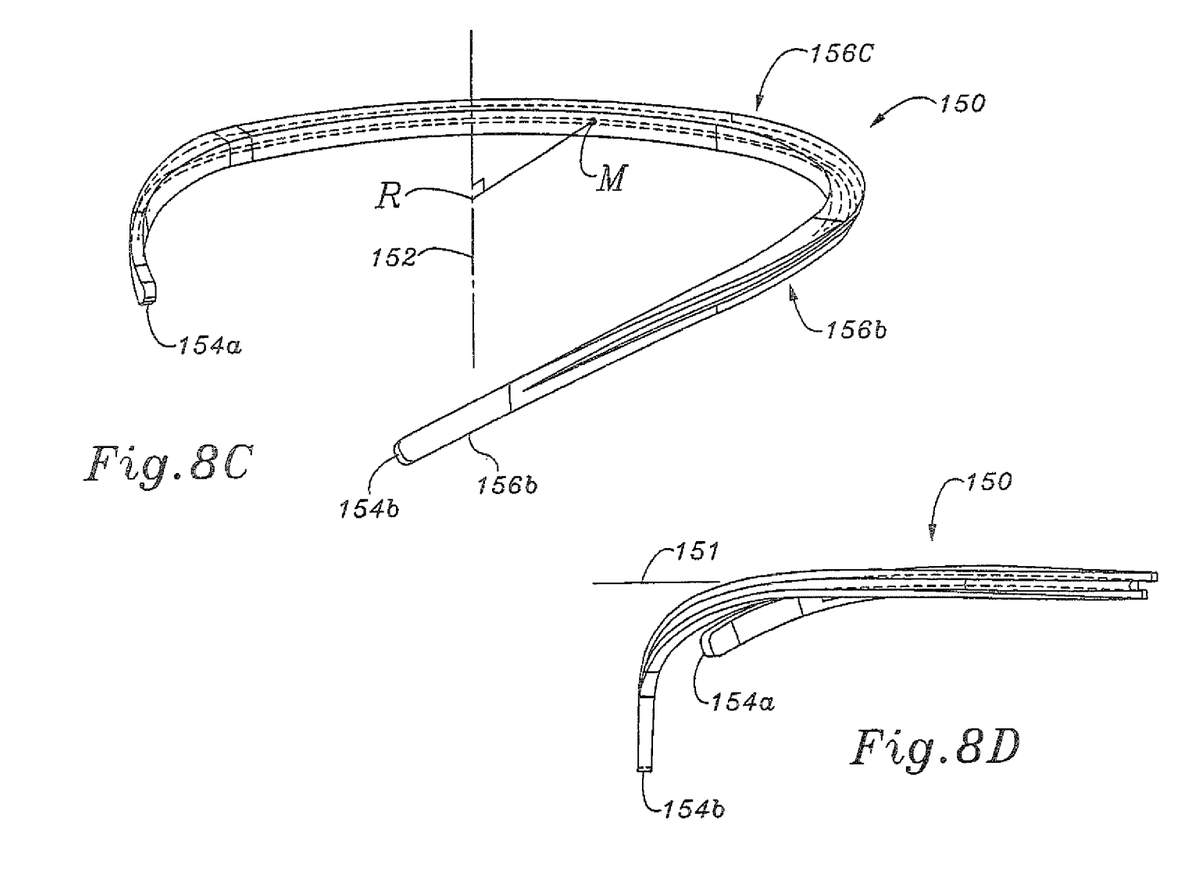

The structural support 150 is generally arranged about an axis 152 and is discontinuous so as to define two free ends 154a, 154b. A majority of the structural support 150 is located generally in an annulus reference plane 151 (see FIG. 8D) perpendicular to the axis 152, and the two free ends 154a, 154b curve away from the plane so as to be offset therefrom. The annulus reference plane 151 is defined as the plane that is perpendicular to the axis 152 at the elevation of the tricuspid annulus. That elevation, in turn, is represented in the drawings by the midpoint of the anterior side 156c, or at least the midpoint of the larger cross-section portion thereof (as detailed below). FIG. 8C illustrates a midpoint M in the anterior side 56c that represents the nominal elevation of the host annulus. A perpendicular line to the axis 152 intersects reference point R. The reference plane is thus perpendicular to the axis 52 through point R.

As seen best in FIG. 8D, the two free ends 154a, 154b are thus axially offset from the reference plane 151 in the same direction, as well as each other. Of course, the free ends 154a, 154b need not be axially offset from each other as is shown, though the ring will still be three-dimensional (that is, the ring is non-planar). For instance, one or both of the free ends 154a, 154b may even curve upward above the reference plane 151. The particular three-dimensional configuration is modeled to fit the natural shape of a tricuspid annulus, or at least to approximate that shape as best as possible, and thus those with an understanding of the tricuspid annulus will realize that a variety of shapes are possible.

Figure 9A:
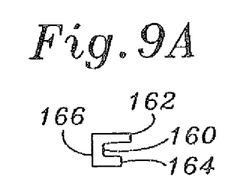
FIGS. 9A-9C are sectional views through the structural support of FIGS. 8A-8D, taken along the section lines indicated in FIG. 8B.
Figure 9B:
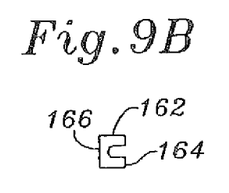

With regard to FIGS. 8B and 9A-9C, the cross-sectional shape of the structural support 150, at least along most of the anterior side 156c, is designed so as to have more flexibility in bending at the free ends 154a, 154b. FIG. 9A is a cross-section through the anterior side 156c and shows a generally C-shaped cross-section with an outwardly-facing groove 160 formed between an upper web 162 and a lower web 164, both extending from an inner base portion 166. The upper web 162 extends slightly farther radially outward than the lower web 164.

Figure 9C:
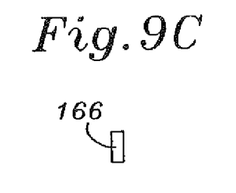

The cross-sectional shape of the structural support 150 changes along its length, from the midpoint M to the free ends 154a, 154b. The transition between the cross-section at the middle of the anterior side 156c and the cross-sections at the two free ends 154a, 154b is gradual, and is reflected in FIGS. 9A-9C. The webs 162, 164 gradually diminish in radial dimension until all that is left is the rectangular base portion 166, as seen in FIG. 9C. Because at both free ends 154a, 154b the radial dimension is smaller than the axial, the ends are more flexible in bending about the central axis 152. It should be mentioned that the properties of the inner ring structural support seen in FIGS. 8A-8D may be attained with other structures, for example, with the multiple concentric bands as described above.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An annuloplasty ring sized and configured for attaching within a valve annulus, comprising:
    a relatively rigid inner body defining an elongated arcuate path, the inner body generally arranged about an axis and being discontinuous so as to define two free ends with a break therebetween, the inner body being formed of a plurality of discrete flat bands extending co-extensively that may flex with respect to one another each having an axial dimension that is smaller than a radial dimension so as to be more flexible in bending about radial lines than about the axis; and
    a suture-permeable matrix closely surrounding the inner body.

2. The annuloplasty ring of claim 1, wherein the bands are each made of Elgiloy.

3. The annuloplasty ring of claim 1, wherein the bands are stacked axially.

4. The annuloplasty ring of claim 1, wherein the bands are concentrically disposed about the axis and spaced radially from each other.

5. The annuloplasty ring of claim 1, wherein the inner body is embedded within the suture-permeable matrix.

6. The annuloplasty ring of claim 5, wherein the suture-permeable matrix includes a portion that conforms to the inner body and an outwardly-extending flange adapted to receive implantation sutures.

7. The annuloplasty ring of claim 1, wherein the inner body is three-dimensional so as not to unduly distort the annulus when secured thereto.

8. The annuloplasty ring of claim 7, wherein a middle portion of the inner body lies within a reference plane and both free ends are axially offset from the reference plane.

9. The annuloplasty ring of claim 7, wherein the two free ends are both axially offset in the same direction from the reference plane.

10. An annuloplasty ring sized and configured for attaching within a tricuspid annulus, comprising:
    a relatively rigid inner body defining an elongated arcuate path, the inner body extending around an axis and being discontinuous so as to define two free ends with a break therebetween, the inner body being formed of a plurality of discrete bands extending co-extensively that may flex with respect to one another each having an axial dimension that is smaller than a radial dimension so as to be more flexible in bending about radial lines than about the axis, the inner body having, in plan view, a curvilinear anterior side terminating in first free end, a relatively straight septal side terminating in a second free end, and a curvilinear posterior side extending between the anterior and septal sides, wherein the inner body is three-dimensional so as not to unduly distort the annulus when secured thereto; and
    a suture-permeable matrix closely surrounding the inner body.

11. The annuloplasty ring of claim 10, wherein the suture-permeable matrix includes a portion that conforms to the inner body and an outwardly-extending flange adapted to receive implantation sutures.

12. The annuloplasty ring of claim 10, wherein a middle portion of the inner body lies within a reference plane.

13. The annuloplasty ring of claim 12, wherein the second free end is axially offset from the reference plane.

14. The annuloplasty ring of claim 13, wherein the first free end is also axially offset from the reference plane.

15. The annuloplasty ring of claim 14, wherein the two free ends are both axially offset in the same direction from the reference plane.

16. The annuloplasty ring of claim 15, wherein the second free end is axially offset farther than the first free end from the reference plane.

17. The annuloplasty ring of claim 10, wherein the bands are stacked axially.

18. The annuloplasty ring of claim 17, wherein the bands are separated by a low friction material so as to be able to more easily flex with respect to one another about radial lines.

19. An annuloplasty ring sized and configured for attaching within a tricuspid annulus, comprising:
    a relatively rigid inner body defining an elongated arcuate path, the inner body extending around an axis and being discontinuous so as to define two free ends with a break therebetween, the inner body being formed of a plurality of discrete axially stacked bands of the same material each of which having an axial dimension that is smaller than a radial dimension so as to be more flexible in bending about radial lines than about the axis, the inner body having, in plan view, a curvilinear anterior side terminating in a first free end, a relatively straight septal side terminating in a second free end, and a curvilinear posterior side extending between the anterior and septal sides, wherein the inner body is three-dimensional such that the septal side that terminates in the second free end is formed in a gentle downward curve so as to be axially offset from a reference plane in which a middle portion of the inner body lies; and
    a suture-permeable matrix closely surrounding the inner body.

20. The annuloplasty ring of claim 19, wherein the suture-permeable matrix includes a portion that conforms to the inner body and an outwardly-extending flange adapted to receive implantation sutures.

21. The annuloplasty ring of claim 19, wherein a majority of the inner body lies within the reference plane.

22. The annuloplasty ring of claim 19, wherein the first free end is also axially offset from the reference plane.

23. The annuloplasty ring of claim 22, wherein the two free ends are both axially offset in the same direction from the reference plane.

24. The annuloplasty ring of claim 23, wherein the second free end is axially offset farther than the first free end from the reference plane.

25. The annuloplasty ring of claim 19, wherein individual bands of the plurality of bands are separated by a low friction material so as to be able to more easily flex with respect to one another about radial lines.

26. The annuloplasty ring of claim 25, wherein the low friction material is Teflon.

\* \* \* \* \*